(12) United States Patent
Kelbauskas et al.

(10) Patent No.: US 10,940,476 B2
(45) Date of Patent: Mar. 9, 2021

(54) DEVICE FOR HIGH-THROUGHPUT MULTI-PARAMETER FUNCTIONAL PROFILING OF THE SAME CELLS IN MULTICELLULAR SETTINGS AND IN ISOLATION

(71) Applicant: Arizona Board of Regents on behalf of Arizona State University, Scottsdale, AZ (US)

(72) Inventors: Laimonas Kelbauskas, Chandler, AZ (US); Honor Glenn, Mesa, AZ (US); Jeff Houkal, Los Angeles, CA (US); Clifford Anderson, Tempe, AZ (US); Yanqing Tian, Tempe, AZ (US); Fengyu Su, Tempe, AZ (US); Deirdre Meldrum, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 213 days.

(21) Appl. No.: 16/095,375

(22) PCT Filed: Apr. 21, 2017

(86) PCT No.: PCT/US2017/028884
§ 371 (c)(1),
(2) Date: Oct. 21, 2018

(87) PCT Pub. No.: WO2017/184998
PCT Pub. Date: Oct. 26, 2017

(65) Prior Publication Data
US 2019/0126275 A1 May 2, 2019

Related U.S. Application Data

(60) Provisional application No. 62/326,455, filed on Apr. 22, 2016.

(51) Int. Cl.
*B01L 3/00* (2006.01)
*B01L 1/00* (2006.01)
*C12M 3/06* (2006.01)
*C12M 1/34* (2006.01)
(Continued)

(52) U.S. Cl.
CPC ....... *B01L 3/502753* (2013.01); *C12M 23/16* (2013.01); *C12M 41/46* (2013.01);
(Continued)

(58) Field of Classification Search
None
See application file for complete search history.

(56) References Cited

U.S. PATENT DOCUMENTS

| 8,748,192 | B2 | 6/2014 | Tian et al. |
| 9,181,375 | B2 | 11/2015 | Tian et al. |

(Continued)

FOREIGN PATENT DOCUMENTS

| WO | 2010022391 A2 | 2/2010 |
| WO | 2010042478 A2 | 4/2010 |

(Continued)

OTHER PUBLICATIONS

Ashili, S.P. et al., "Automated platform for multiparameter stimulus response studies of metabolic activity at the single-cell level," Proceedings of SPIE, vol. 7929, 2011, 12 pages.
(Continued)

*Primary Examiner* — Nathan A Bowers
(74) *Attorney, Agent, or Firm* — Withrow & Terranova, P.L.L.C.

(57) ABSTRACT

A device for high-throughput multi-parameter functional profiling of the same cells in multicellular settings and in isolation is provided. In certain aspects, an integrated microfluidic device for multi-parameter metabolic and other phenotypic profiling of live biological cells is useable with: 1) multicellular clusters or small biopsy tissue samples, 2)
(Continued)

cultures of the constituent cells obtained after cluster/tissue dissociation, and 3) the same constituent single cells in isolation. The approach enables study of the effects of multicellular complexity, such as in response to treatment, pathogens, stress, or other factors concerning disease origination and progression. Measurements may be performed on single cells or multicellular populations or tissues in the same assay at the same time.

15 Claims, 6 Drawing Sheets

(51) Int. Cl.
*C12Q 1/02* (2006.01)
*G01N 33/487* (2006.01)

(52) U.S. Cl.
CPC . *B01L 2200/0668* (2013.01); *B01L 2400/086* (2013.01); *C12Q 1/02* (2013.01); *G01N 33/48735* (2013.01)

(56) References Cited

U.S. PATENT DOCUMENTS

| | | | |
|---|---|---|---|
| 9,222,870 B2* | 12/2015 | Di Carlo | G01N 15/1468 |
| 9,297,784 B2* | 3/2016 | Molho | G01N 27/44756 |
| 9,410,970 B2 | 8/2016 | Tian et al. | |
| 9,597,026 B2 | 3/2017 | Meldrum et al. | |
| 9,889,445 B2* | 2/2018 | Chapman | G01N 33/5047 |
| 10,022,718 B2 | 7/2018 | Martineau et al. | |
| 10,156,573 B2 | 12/2018 | Tian et al. | |
| 10,162,162 B2 | 12/2018 | Wang et al. | |
| 10,221,443 B2 | 3/2019 | Meldrum et al. | |
| 10,391,485 B2 | 8/2019 | Meldrum et al. | |
| 10,471,426 B2 | 11/2019 | Martineau et al. | |
| 10,590,155 B2 | 3/2020 | Kong et al. | |
| 2007/0166816 A1 | 7/2007 | Campbell et al. | |
| 2009/0215194 A1* | 8/2009 | Magni | B01L 3/502707 436/174 |
| 2010/0003666 A1* | 1/2010 | Lee | C12Q 1/6816 435/5 |
| 2011/0045994 A1* | 2/2011 | Voldman | G01N 33/5005 506/7 |
| 2012/0135452 A1 | 5/2012 | Shuler et al. | |
| 2012/0231533 A1 | 9/2012 | Holl et al. | |
| 2012/0301913 A1 | 11/2012 | Youngbull et al. | |
| 2014/0378352 A1 | 12/2014 | Daridon | |
| 2015/0253333 A1 | 9/2015 | Tian et al. | |
| 2015/0298129 A1* | 10/2015 | Dugan | B01L 3/50851 435/286.1 |
| 2016/0084750 A1 | 3/2016 | Wang et al. | |
| 2016/0202247 A1 | 7/2016 | Tian et al. | |
| 2016/0215254 A1 | 7/2016 | Meldrum et al. | |
| 2018/0264468 A1 | 9/2018 | Anderson et al. | |
| 2018/0334700 A1 | 11/2018 | Messner et al. | |
| 2019/0177784 A1 | 6/2019 | Martineau et al. | |
| 2019/0346361 A1 | 11/2019 | Meldrum et al. | |
| 2019/0360984 A1 | 11/2019 | Zhang et al. | |
| 2020/0047182 A1 | 2/2020 | Meldrum et al. | |
| 2020/0049694 A1 | 2/2020 | Anderson et al. | |
| 2020/0058140 A1 | 2/2020 | Meldrum et al. | |
| 2020/0063197 A1 | 2/2020 | Meldrum et al. | |

FOREIGN PATENT DOCUMENTS

| | | |
|---|---|---|
| WO | 2010062654 A2 | 6/2010 |
| WO | 2012112440 A2 | 8/2012 |
| WO | 2014153651 A1 | 10/2014 |
| WO | 2015048009 A1 | 4/2015 |
| WO | 2017049122 A1 | 3/2017 |
| WO | 2017062807 A1 | 4/2017 |
| WO | 2017083817 A1 | 5/2017 |
| WO | 2017087473 A1 | 5/2017 |
| WO | 2017151978 A1 | 9/2017 |
| WO | 2018013948 A1 | 1/2018 |
| WO | 2018027236 A1 | 2/2018 |
| WO | 2018136794 A1 | 7/2018 |
| WO | 2018157064 A1 | 8/2018 |
| WO | 2018160998 A1 | 9/2018 |
| WO | 2018213269 A1 | 11/2018 |
| WO | 2019046452 A1 | 3/2019 |

OTHER PUBLICATIONS

Calorini, L. et al., "Environmental control of invasiveness and metastatic dissemination of tumor cells: the role of tumor cell-host cell interactions," Cell Communication and Signaling, vol. 8, Issue 1, Dec. 2010, 10 pages.

Erez, N. et al., "Cancer-Associated Fibroblasts Are Activated in Incipient Neoplasia to Orchestrate Tumor-Promoting Inflammation in an NF-κB-Dependent Manner," Cancer Cell, vol. 17, Issue 2, Feb. 17, 2010, Elsevier Inc., pp. 135-147.

Gatenby, R.A. et al., "Why Do Cancers Have High Aerobic Glycolysis?" Nature Reviews Cancer, vol. 4, Issue 11, Nov. 2004, pp. 891-899.

Hanahan, D. et al., "Hallmarks of Cancer: The Next Generation," Cell, vol. 144, Mar. 4, 2011, Elsevier Inc., pp. 646-674.

Kelbauskas, L. et al., "A novel method for multiparameter physiological phenotype characterization at the single-cell level," Proceedings of SPIE, vol. 7902, 2011, 9 pages.

Kelbauskas, L. et al., "A platform for high-throughput bioenergy production phenotype characterization in single cells," Scientific Reports, vol. 7, Article 45399, Mar. 28, 2017, 13 pages.

Kelbauskas, L. et al., "Platform for combined analysis of functional and biomolecular phenotypes of the same cell," Scientific Reports, vol. 7, Article 44636, Mar. 16, 2017, 11 pages.

Laconi, E. et al., "The microenvironments of multistage carcinogenesis," Seminars in Cancer Biology, vol. 18, Issue 5, 2008, Elsevier Ltd., pp. 322-329.

Lahar, N. et al., "Intestinal Subepithelial Myofibroblasts Support in vitro and in vivo Growth of Human Small Intestinal Epithelium," PLoS ONE, vol. 6, Issue 11, Nov. 17, 2011, 9 pages.

Lovchik, R.D. et al., "Overflow Microfluidic Networks for Open and Closed Cell Cultures on Chip," Analytical Chemistry, vol. 82, No. 9, May 1, 2010, American Chemical Society, pp. 3936-3942.

Polyak, K. et al., "Co-evolution of tumor cells and their microenvironment," Trends in Genetics, vol. 25, Issue 1, Jan. 2009, Elsevier Ltd., pp. 30-38.

Solaini, G. et al., "Oxidative phosphorylation in cancer cells," Biochimica et Biophysica Acta (BBA)—Bioenergetics, vol. 1807, Issue 6, 2011, Elsevier B.V., pp. 534-542.

Staal, E. et al., "The stromal part of adenocarcinomas of the oesophagus: Does it conceal targets for therapy?" European Journal of Cancer, vol. 46, Issue 4, 2010, Elsevier Ltd., pp. 720-728.

Visvader, J.E. et al., "Cancer stem cells in solid tumours: accumulating evidence and unresolved questions," Nature Reviews Cancer, vol. 8, Issue 10, Oct. 2008, MacMillan Publishers Limited, pp. 755-768.

Wang, D. et al., "Aberrant Epithelial-Mesenchymal Hedgehog Signaling Characterizes Barrett's Metaplasia," Gastroenterology, vol. 138, Issue 5, May 2010, AGA Institute, pp. 1810-1822.

Wang, D. et al., "Single cell analysis: the new frontier in 'omics,'" Trends in Biotechnology, vol. 28, Issue 6, 2010, Elsevier Ltd., pp. 281-290.

International Search Report and Written Opinion for International Patent Application No. PCT/US17/28884, dated Jul. 26, 2017, 10 pages.

International Preliminary Report on Patentability for International Patent Application No. PCT/US17/28884, dated Nov. 1, 2018, 9 pages.

U.S. Appl. No. 16/323,393, Martineau et al., filed Feb. 5, 2019.
U.S. Appl. No. 16/479,729, Meldrum et al., filed Jul. 22, 2019.
U.S. Appl. No. 16/631,040, Johnson et al., filed Jan. 14, 2020.

* cited by examiner

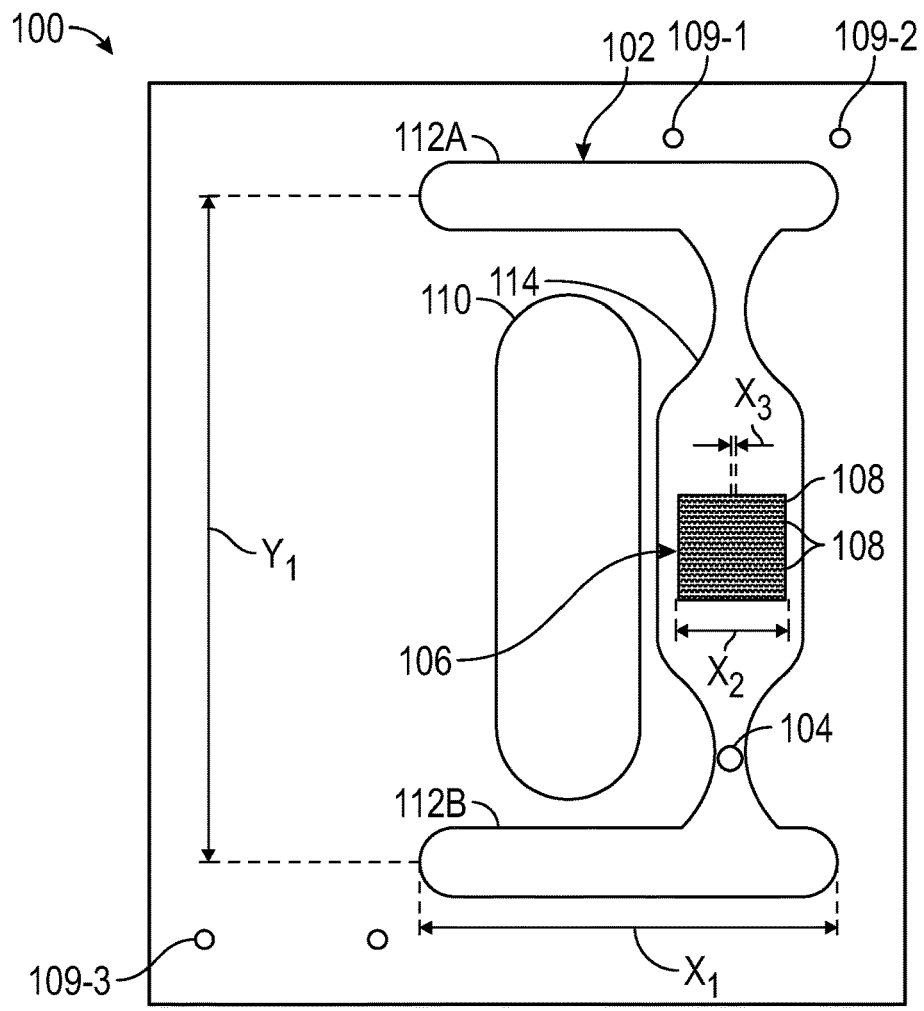
FIG. 1A
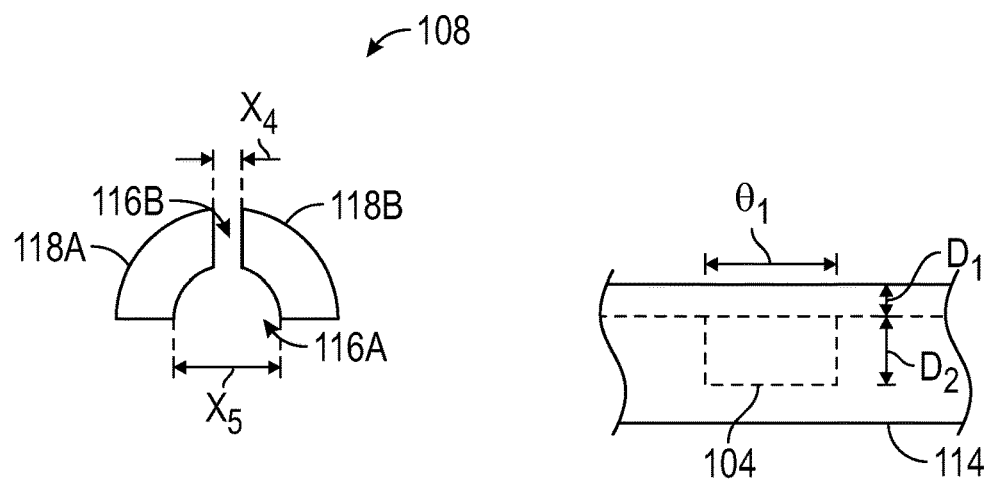
FIG. 1B
FIG. 1C

DEVICE FOR HIGH-THROUGHPUT MULTI-PARAMETER FUNCTIONAL PROFILING OF THE SAME CELLS IN MULTICELLULAR SETTINGS AND IN ISOLATION

STATEMENT OF RELATED APPLICATION(S)

This application is a 35 U.S.C. § 371 national phase filing of International Application No. PCT/US2017/028884 filed on Apr. 21, 2017, and claims the benefit of U.S. Provisional Patent Application No. 62/326,455, filed on Apr. 22, 2016, wherein the disclosures of the foregoing applications are hereby incorporated by reference herein in their respective entireties. This application also relates to U.S. Provisional Patent Application No. 62/464,125 filed on Feb. 27, 2017, the disclosure of which is hereby incorporated by reference herein in its entirety.

GOVERNMENT RIGHTS IN INVENTION

This invention was made with government support under P50 HG002360 awarded by the National Institutes of Health. The U.S. government has certain rights in the invention.

TECHNICAL FIELD

This disclosure relates to devices and methods for profiling live biological cells.

BACKGROUND

The fundamental decision-making entity in a biological organism is the cell. Recent advances reveal that intercellular heterogeneity is an essential characteristic of all naturally occurring cell populations, and is also reflected in cell lines adapted to in vitro culture. This suggests that traditional, population-averaged cellular assays may fail to capture the actual range of cellular states or responses to stimuli. Intercellular variability is directly relevant to human health since small subpopulations of cells can have a profound impact on health and disease. For example, lineage-restricted stem cells in the gastrointestinal tract represent a small minority of the epithelial cells, but are responsible for generating the entire cell layer which is composed of at least five cell types and is continuously renewed. As another example, cancer is characterized by extraordinary heterogeneity, perhaps from its initiation. A typical tumor is composed of a mix of genetic and phenotypic cell types in various stages of progression and adapted to different microenvironments. This variability has a profound impact on the effectiveness of therapeutic interventions. A cancer drug that shrinks a tumor to below the level of detection may ultimately fail to eradicate disease if it is ineffective against a few cells (or possibly one cell) having the capacity to re-initiate tumor growth. Therapeutic intervention frequently eradicates all detectable tumors, but the patient later relapses with a much more aggressive disease. What differences enabled a few cancer cells to resist treatment and recapitulate the pathology? What phenotypic signatures could identify these cells and enable therapeutic intervention?

Another emerging theme in biomedical and clinical research is the importance of the microenvironment in cell state and decision making. Cells function in the context of homotypic and/or heterotypic interactions with neighboring cells mediated by direct contact and/or diffusible factors. Therefore, the multicellular in vivo complexity of the cell behavior is not necessarily recapitulated in cultures of dissociated cells.

Traditional inquiries into cellular states and processes have relied upon population-averaged data obtained from tens of thousands to millions of cells. Such approaches were used because the object of interest—namely, the cell—was too tiny to measure directly. Although such techniques have yielded much useful information, these approaches are limited in that they cannot resolve the contributions of individual cells. This precludes the detection of differing responses or states in sub-populations of cells under study, and disallows detection of signals of rare or unique cells. Flow cytometry and fixed cell microscopy are effective methods for gathering information with single cell resolution; however, these techniques are limited in that they provide only a snapshot of cell state. Live cell imaging methods employing fluorescent probes can provide more or less quantitative information on intracellular targets, and fluorescent protein-based techniques can report on cellular processes and molecular interactions. One caveat with these strategies is that they necessarily introduce some degree of intracellular perturbation. Additionally, these strategies are not useful for measurement of transmembrane fluxes of diffusible analytes that are produced or consumed. Even if such species could be detected, no method has existed to identify the contributing effects of individual cells.

Recent insights into the significance of cellular heterogeneity have fueled interest in efficient, quantitative single cell analytical approaches. Due to significant cell-to-cell heterogeneity, a clear understanding of cellular functions under physiologic, pathologic, and therapeutic conditions requires analyses with single cell resolution. However, interrogation of individual, isolated cells may fail to be fully relevant to human health, because in vivo cells are in constant physical and diffusional contact with other cells and with extracellular matrix components in a specific structural organization. This microenvironment supports a constant flow of information between cells which influences cellular state. For example, in healthy intestinal epithelium, lineage restricted stem cells rely on cues from stromal cells surrounding the stem cell niche in order to proliferate.

There is an emerging understanding that cancer is not only a disease of what we typically identify as the "cancer cell". Rather, cancer is a set of pathological interactions between various cell types that together form a niche required for carcinogenesis and progression. Microenvironment interactions have been implicated in every stage of carcinogenesis from initiation to progression and metastasis. An aspect of the microenvironment particularly relevant to health and disease is mediation of cellular metabolism. There is a large body of ongoing research implicating local inflammation as a driving force in oncogenesis. Inflammation causes local hypoxia that triggers hypoxia response signaling, which, in turn, downregulates oxidative phosphorylation and boosts glycolysis. This metabolic shift is recognized as a hallmark of cancer and has been identified as an initiating factor. It would be desirable to provide a sensitive measure of metabolic signatures of cells in both their in situ microenvironment and individually, to bridge a gap in understanding between the attributes of individual cells and the function of intact tissues.

The degree to which metabolic functions and the state of specific cells depend on micro-environmental interactions is highly variable and is likely context-dependent. The device disclosed herein allows researchers to systematically evaluate the effects of cellular heterogeneity and in situ interactions on cellular metabolism, enabling integrated analysis of multicellular structures and their constituent individual cells. One transformative application of this device is that it enables direct evaluation of the relevance of measuring metabolic responses in dissociated or isolated cells versus intact multicellular units. This analysis is applicable to a wide range of cell and tissue types and will accommodate a nearly unlimited variety of test conditions or chemical stimuli. The proposed integrated experimental platform is simple to use and is compatible with many commercial imaging instruments already in use in numerous research and clinical laboratories.

Cell metabolism is known to be one of the core factors influencing normal cell functioning and pathogenic alterations, including diseased states such as cancer. In vivo cellular metabolism is also critically dependent on the microenvironment. Therefore, studying metabolic parameters of cells in situ can provide crucial insights into factors and mechanisms regulating normal cell functioning and associated with disease onset. However, in situ metabolic profiling with high spatial and temporal resolution is challenging because cells of interest are difficult to access in terms of both delivery of contrast agents/reporters and signal detection.

Some technologies permit metabolic rate measurements of bulk (including multicellular clusters) samples; however, the lower limit in this approach is several thousands of cells and cannot reach single cell sensitivity. Moreover, these technologies may be currently limited to the measurement of oxygen consumption rates and/or extracellular acidification rates, and does not permit imaging of the cells being studied.

It would be desirable to permit metabolic parameters to be studied in a non-invasive manner without molecular or chemical manipulation of cells. It would also be desirable to permit in situ analysis of metabolic parameters with spatial and temporal resolution, in dissociated bulk cell populations and at the single cell level. Subject matter disclosed herein overcomes limitations associated with existing devices and methods.

SUMMARY

In certain aspects, the present disclosure describes an integrated microfluidic device for multi-parameter metabolic and other phenotypic profiling of live biological cells in three different structural settings: 1) multicellular clusters or small biopsy tissue samples, 2) cultures of the constituent cells obtained after cluster/tissue dissociation, and 3) the same constituent single cells in isolation. This approach enables the unique capability of studying the effects of multicellular complexity, such as in response to treatment, pathogens, stress, or other factors in the context of disease origination and progression. The approach also permits measurements to be performed on single cells or multicellular populations or tissues in the same assay at the same time.

In certain embodiments, devices and methods disclosed herein are non-invasive and do not rely upon molecular or chemical manipulation of cells. In certain embodiments, an integrated microfluidic device combines analysis of metabolic parameters with spatial and temporal resolution in situ, in dissociated bulk cell populations, and at the single cell level. In certain embodiments, such a device provides the capability to quantify alterations in metabolic parameters in response to various stimuli, such as hypoxia or exposure to therapeutic agents. The devices and methods are simple to employ in various research laboratory settings and broadly applicable to different types of samples.

In certain embodiments, two analytic techniques are integrated, thereby enabling a direct comparison of metabolic cell state between native, multicellular structures and their constituent cells. Contributions from simple cell-cell proximity and microenvironment architecture are also de-confounded. The power to interrogate both metabolism and gene expression in single, identifiable cells and relate these data to intact multicellular functional tissue units represents a paradigm shift in single cell analysis.

In certain embodiments, devices disclosed herein overcome challenges of directly correlating metabolic function of intact multicellular structures such as biopsy tissue samples, their constituent cells after dissociation into a cell culture, and the individual constituent cells in isolation. In certain embodiments, a device is configured to perform such measurements on both bulk cell cultures and single cells of the same type. The analysis is non-invasive and non-perturbing since it relies on extracellular (e.g., optical) sensors.

In one aspect, a proposed microfluidic device for multi-parameter phenotypic profiling of live or fixed individual cells in isolation and within complex multicellular structures in a same assay includes at least a bottom substrate that may include a microfluidic structure or chip. The bottom substrate defines a microfluidic channel containing a plurality of split-walled cell trap structures. The bottom substrate further defines a "milliwell" arranged for at least selective fluid communication with the microfluidic channel. In certain embodiments, the microfluidic device further includes a top substrate defining a lid configured to mate with and seal the bottom substrate. In certain embodiments, one of the bottom substrate or the top substrate is configured to be moved relative to the other of the bottom substrate or the top substrate between a first position and a second position, to permit said mating with and sealing between at least portions of the bottom substrate and the top substrate. In certain embodiments, the microfluidic device further includes a top substrate defining an array of lids arranged to align with the plurality of split-walled cell trap structures, and defines a milliwell lid arranged to align with the milliwell. In certain embodiments, one of the bottom substrate or the top substrate is configured to be moved relative to the other of the bottom substrate and the top substrate between a first position and a second position, to permit mating and sealing between at least portions of the bottom substrate and the top substrate. Such movement may include any combination of one or multiple steps such as horizontal translation, vertical translation, lateral translation, and rotation, performed in any suitable order. In certain embodiments, movement of one of the bottom substrate or the top substrate includes vertical translation followed by lateral translation, or horizontal translation followed by vertical translation.

In certain embodiments, the array of lids includes an array of lips defining a plurality of microwells, the milliwell comprises a greater volume than the plurality of microwells, and the plurality of split-walled cell trap structures is arranged to be registered with and at least partially received by the plurality of microwells when the microfluidic device is in one of the first position or the second position. In certain embodiments, a gap is provided between the bottom substrate and the top substrate along each lip of the array of lips to permit fluid to flow past or through the plurality of split-walled cell trap structures when the microfluidic device is in one of the first position or the second position. In certain embodiments, the milliwell is centrally arranged relative to the plurality of split-walled cell trap structures.

In certain embodiments, each cell trap structure of the plurality of split-walled cell trap structures includes an open upstream end sized to receive at least one cell, and includes a downstream opening configured to inhibit passage of at least one cell while permitting passage of a liquid medium. In certain embodiments, each cell trap structure of the plurality of split-walled cell trap structures is configured to receive only a single cell.

In certain embodiments, an array of sensors is arranged in at least one of the bottom substrate or the top substrate, wherein the array of sensors is in sensory communication with the plurality of microwells.

In certain embodiments, the microfluidic device is configured for multi-parameter characterization of cellular phenotypes of cells in tissue or other multicellular structures and the same individual cells in isolation followed by end-point analysis of biomolecular profiles of the same cells. In certain embodiments, the end-point analysis includes at least one of DNA sequencing, gene expression analysis, or protein expression analysis.

In another aspect, a microfluidic device for multiparameter phenotypic profiling of live or fixed individual cells in isolation and within complex multicellular structures in a same assay includes a first substrate and a second substrate. The first substrate defines a milliwell and an array of microwells, wherein the milliwell includes a greater volume than each microwell of the array of microwells. The second substrate includes a lid arranged to cover the milliwell and an array of lids to cover the array of microwells. One of the first substrate or the second substrate is configured to be moved relative to the other of the first substrate or the second substrate between a first position and a second position, to permit the milliwell and the array of microwells to be selectively sealed. In certain embodiments, the microfluidic device further includes a plurality of split-walled cell trap structures arranged to be selectively registered with and disposed within the array of microwells when the microfluidic device is in one of the first position or the second position. In certain embodiments, each cell trap structure of the plurality of split-walled cell trap structures is configured to receive only a single cell. In certain embodiments, movement of one of the first substrate or the second substrate includes vertical translation followed by lateral translation, or horizontal translation followed by vertical translation.

In certain embodiments, a gap is provided between the first substrate and the second substrate along a lip of each lid of the array of lids to permit fluid to flow past or through the plurality of split-walled cell trap structures when the microfluidic device is in one of the first position or the second position. In certain embodiments, the milliwell is centrally arranged relative to the plurality of split-walled cell trap structures. In certain embodiments, each cell trap structure of the plurality of split-walled cell trap structures includes an open upstream end sized to receive at least one cell, and includes a downstream opening configured to inhibit passage of at least one cell while permitting passage of a liquid medium.

In certain embodiments, the microfluidic device further includes an array of sensors arranged in at least one of the first substrate or the second substrate, wherein the array of sensors is in sensory communication with the array of microwells.

In certain embodiments, the microfluidic device is configured for multi-parameter characterization of cellular phenotypes of cells in tissue or other multicellular structures and the same individual cells in isolation followed by end-point analysis of biomolecular profiles of the same cells. In certain embodiments, the end-point analysis includes at least one of DNA sequencing, gene expression analysis, or protein expression analysis.

In certain embodiments, a microfluidic device comprises two substrates or layers that may embody microfluidic structures or chips. A bottom substrate or layer includes a "milliwell" to analyze intact multicellular structures, and an array of microwells in which single cells are assayed. A top substrate or layer includes a lid patterned with fluorescent sensors that respond to soluble analytes such as oxygen or glucose, changes in pH, or any other types of sensors and combinations thereof. In a closed configuration, the top substrate or layer (or lid) forms a hermetic seal around each of the cell-containing microwells, permitting the sensor array to be read. In certain embodiments, substrates or layers of the device can be made of glass or other optically transparent materials to enable simultaneous imaging of cell clusters and cells using various microscopy modalities. In certain embodiments, a microfluidic device represents an integrated tool that will allow researchers to bridge the gap in understanding between the attributes of individual cells and the function of intact tissues.

In certain embodiments, multi-parameter characterization of cellular phenotypes of cells in tissue or other multicellular structures and the same individual cells in isolation may be performed, followed by end-point analysis of biomolecular profiles of the same cells. In certain embodiments, such end-point analysis comprises at least one of DNA sequencing, gene expression analysis, or protein expression analysis.

In certain embodiments, a device disclosed herein can be used for identifying small populations or individual rare cells with abnormal function and/or response to stress that are responsible for pathogenesis and disease recurrence. As a means for multi-parameter multiplexed analysis of transmembrane fluxes and cell state in general, such a device and associated methods can be utilized in clinical and pharmacological settings for the following applications: (1) research involving measurements of metabolism, gene expression, and more in the context of multicellular complexity; (2) stimulus-response experiments where the stimulus includes environmental changes, infection, perturbagens, drugs, genomic alterations, etc.; (3) drug screening and response studies (e.g. pharmacokinetics); (4) early disease detection and screening; (5) risk assessment for disease progression (e.g., premalignant to malignant progression in cancer); (6) therapeutic targets identification and validation; (7) biosignature development and validation; and (8) stress response studies.

BRIEF DESCRIPTION OF THE DRAWINGS

FIG. 1A is a top plan view of a bottom layer of a microfluidic device for integrated metabolic profiling of intact tissue samples, their dissociation, and single-cell analysis.

FIG. 1B is a top plan view of a Pachinko-type single cell trap of the bottom layer of the microfluidic device of FIG. 1A.

FIG. 1C is a side view of a milliwell of the bottom layer of the microfluidic device of FIG. 1A.

DETAILED DESCRIPTION

In certain aspects, the present disclosure describes an integrated microfluidic device for multi-parameter metabolic profiling and other phenotypic profiling of live biological cells in three different structural settings: 1) multicellular clusters or small biopsy tissue samples, 2) cultures of the constituent cells obtained after cluster/tissue dissociation, and 3) the same constituent single cells in isolation.

To perform metabolic parameter measurements of multi-cellular structures, their dissociated cells, and corresponding isolated single cells, a microfluidic device according to at least certain embodiments is configured to perform all necessary steps on-site, i.e., without the need to transfer small sample volumes between vials, pipette tips, etc. In certain embodiments, single-cell handling and metabolic phenotype characterization is performed with a microfluidic device using integrated extracellular (e.g., fluorescent or other) sensors. In certain embodiments, a microfluidic device lid may be patterned with fluorescent sensors or other optical sensors that respond to soluble analytes such as oxygen or glucose, changes in pH, or any other suitable analyte(s) or detectable parameter(s) and combinations thereof. The sensor type is not limited in any way in its nature, molecular structure or composition. In certain embodiments, both in situ cells (in native, multicellular structures) and isolated single cells may be analyzed in hermetically sealed wells utilizing sensors (e.g., optical sensors) deposited inside the wells and/or arranged outside the wells. In certain embodiments, measurements may be performed on single cells or multicellular populations or tissues in the same assay at the same time.

Figure 2A:
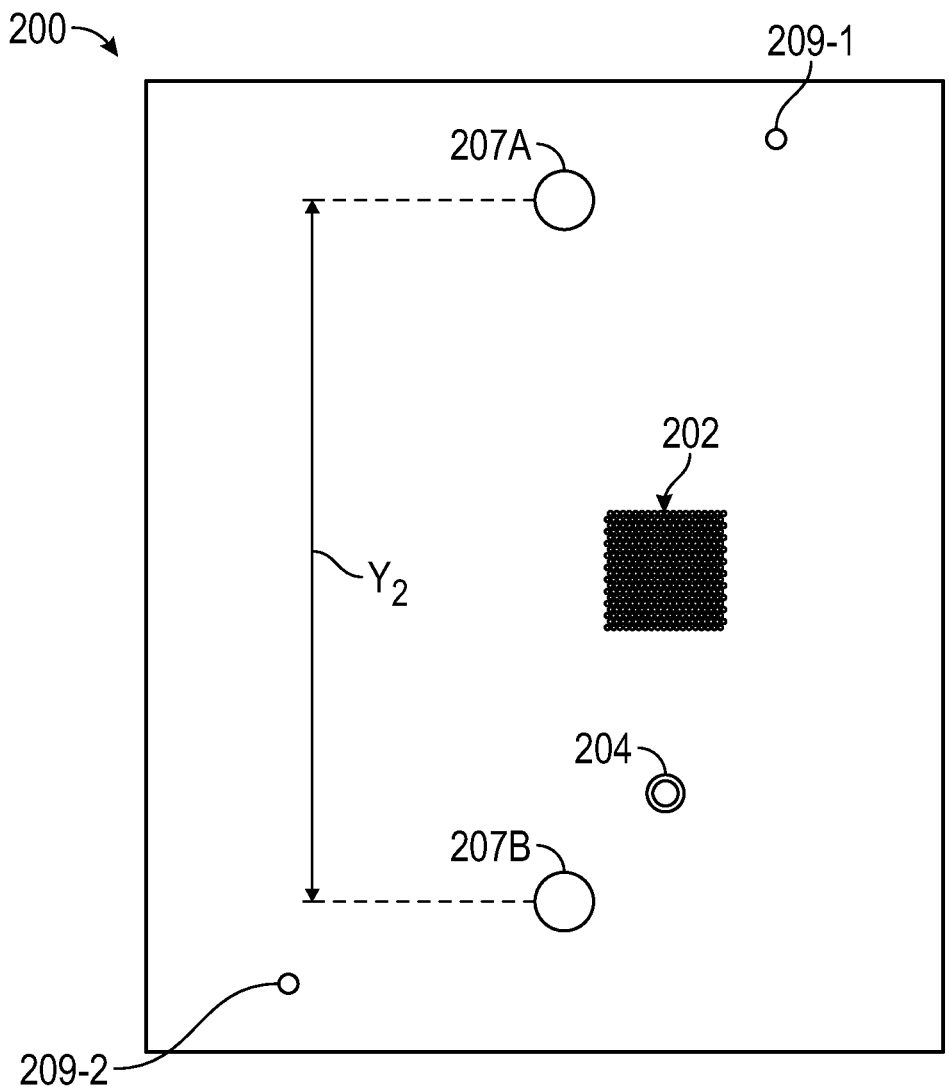
FIG. 2A is a top plan view of a top layer of the microfluidic device configured to engage the bottom layer of FIG. 1A.
Figures 2B, 2C:
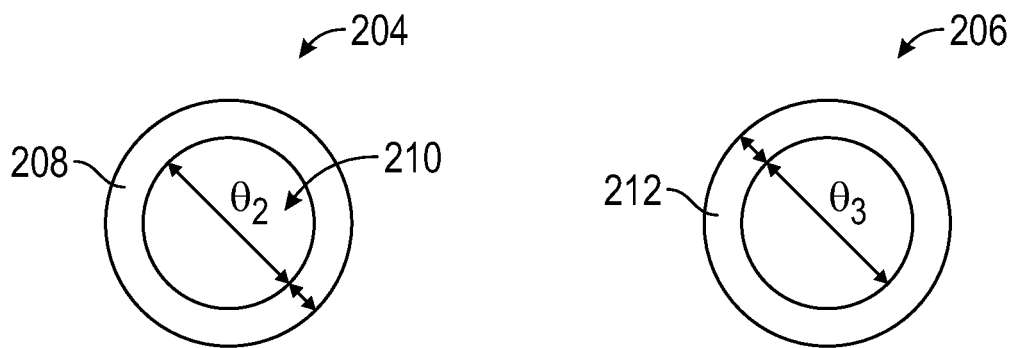
FIG. 2B is a top plan view of a lid of the top layer of FIG. 2A configured to enclose a Pachinko-type single cell trap of the bottom layer of FIG. 1A.
FIG. 2C is a top plan view of a lid of the top layer of FIG. 2A configured to enclose a milliwell of the bottom layer of FIG. 1A.
Figure 3A:
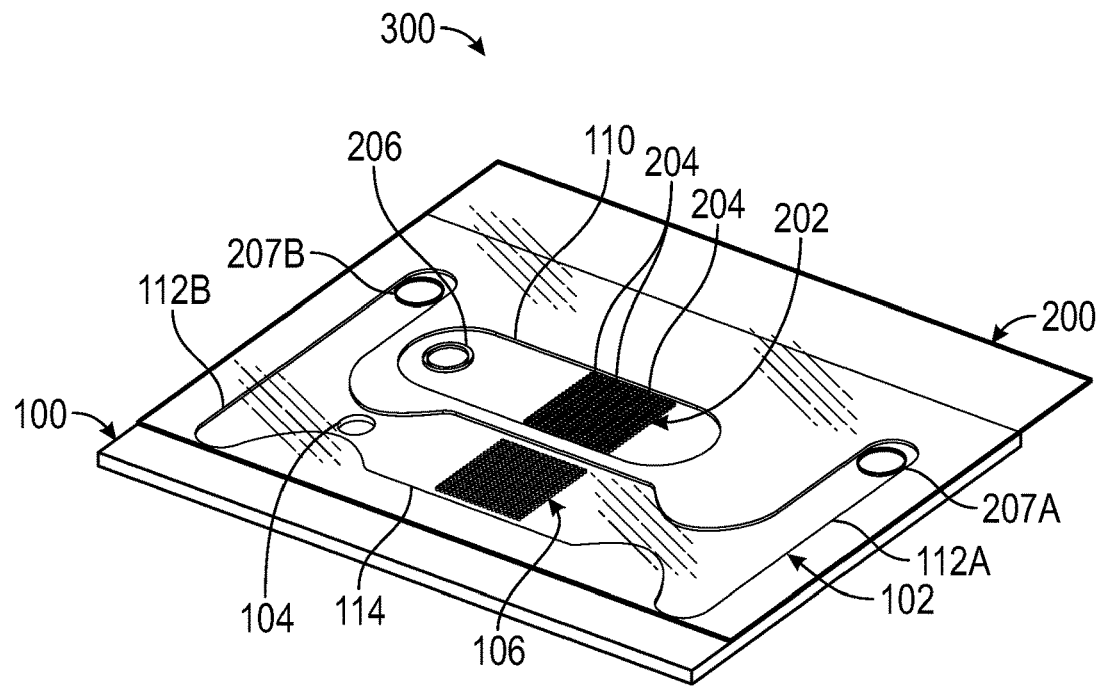
FIG. 3A is a perspective view of a microfluidic device as described herein in an open state.
Figure 3B:
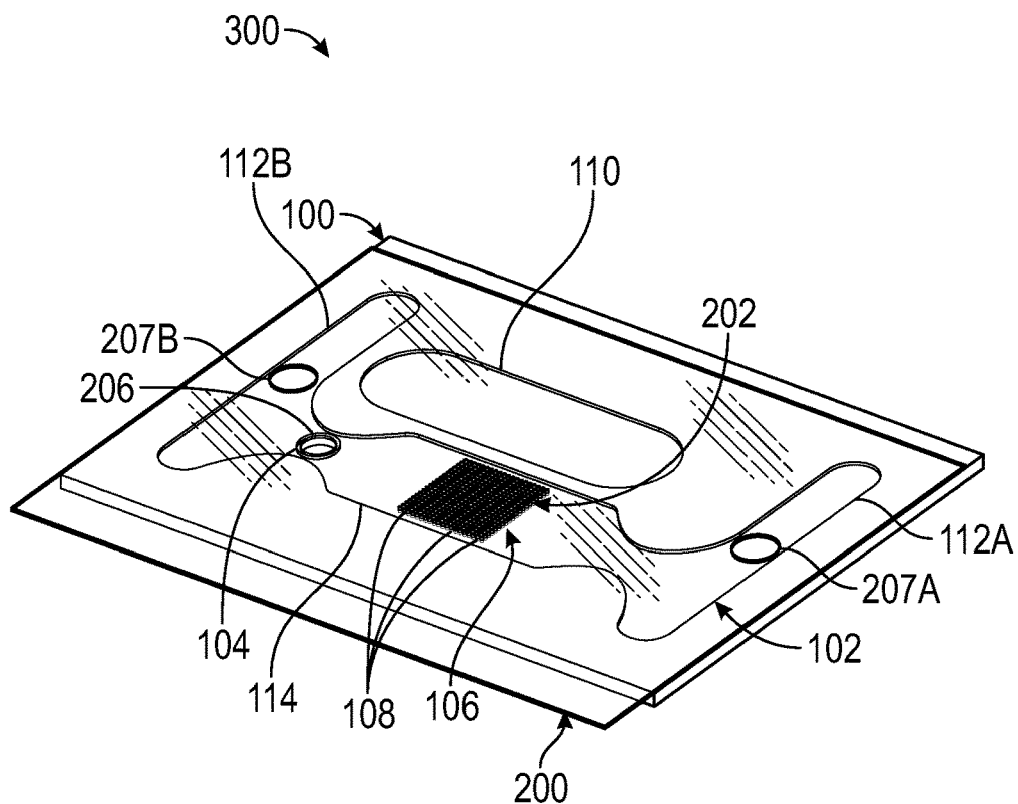
FIG. 3B is a perspective view of the microfluidic device of FIG. 3A in a closed state.

Referring to FIGS. 1A-3B, in certain embodiments, a microfluidic device 300 may include two major parts. FIGS. 1A-1C illustrate a bottom part 100 (also referred to as a bottom layer, bottom substrate, etc.) of the microfluidic device 300, and FIGS. 2A-2C illustrate a top part 200 (also referred to as a top layer, top substrate, etc.) of the microfluidic device 300. FIGS. 3A and 3B illustrate the microfluidic device 300 in an open state and a closed state, respectively. Note that in these figures, and the figures throughout the disclosure, are not necessarily to scale and are provided for illustrative purposes only.

Referring to FIGS. 1A-1C, the bottom part 100 includes microfluidic channels 102 (also referred to as media flow channels), a milliwell 104 for confinement of large multicellular structures, an array 106 of Pachinko-type single cell traps 108, and a receiving (recessed) chamber 110 arranged to be covered by a lid (described hereinafter in connection with FIGS. 2A-2C). In certain embodiments, the bottom part 100 also includes one or more fiducials 109-1 to 109-3 to promote alignment of the bottom part 100 with the top part 200 in an open state and in a closed state (as described hereinafter in connection with FIGS. 2A-2C). In certain embodiments, the microfluidic channels 102 may include two parallel media flow channel portions 112A, 112B connected by a transverse channel 114, which is transversely arranged (e.g., having a depth of about 20 μm) and contains the Pachinko-type single cell traps 108. In certain embodiments, the two parallel media flow channel portions 112A, 112B each have a length $X_1$ (e.g., 15 mm) and are separated from one another by a distance $Y_1$ (e.g., 21.5 mm). In certain embodiments, the receiving chamber 110 has a depth of about 20 μm. In certain embodiments, the array 106 has a width $X_2$ of about 4 mm, and each single cell trap 108 within the array 106 is longitudinally separated from each other single cell trap 108 by a distance $X_3$ of about 200 μm.

Referring to FIG. 1B, each Pachinko-type single cell trap 108 includes an open upstream end 116A sized to receive a cell, and includes a downstream opening 116B (also referred to as a downstream end) configured to inhibit passage of at least one cell while permitting passage of a liquid (e.g., aqueous) medium. In particular, each Pachinko-type single cell trap 108 may include a split-walled compartment including the open upstream end 116A (also referred to as an upstream opening), defined by two 10 micron high curved wall portions 118A, 118B separated by a distance $X_4$ of about 3 microns at the downstream opening 116B, and separated by a distance $X_5$ of about 10 microns at the open upstream end 116A. In certain embodiments, the Pachinko-type single cell traps 108 serve the purpose of trapping individual cells with high efficiency, with each individual cell trap 108 being designed to allow only one cell to be caught.

Referring to FIG. 1C, in certain embodiments the microfluidic channels 102 (including the media flow channel portions 112A, 112B and/or the transverse channel 114) may have a depth $D_1$ (e.g., 20 μm) and the milliwell 104 positioned within the transverse channel 114 may have a depth $D_2$ (e.g., 200 μm) and a diameter $\theta_1$ (e.g., 800 μm).

Referring to FIGS. 2A-2C, the top part 200 of the microfluidic device 300 contains an array 202 of lids 204 (or a single lid 204) arranged to align with the array 106 of Pachinko-type single cell traps 108 defined in the bottom part 100 of the microfluidic device 300. The top part 200 further contains a lid 206 for the milliwell 104 (shown in FIG. 2C). The top part 200 additionally includes one or more media flow channel ports 207A, 207B separated from one another by a distance $Y_2$ (to align with the media flow channel portions 112A, 112B.

FIG. 2B is a top plan view of a representative lid 204 of the array 202 of lids 204. The lid 204 includes a cylindrical lip 208 (e.g., having a lip height of about 20 μm, a lip width of about 20 μm, and a diameter $\theta_2$ of about 80 μm) defining a microwell 210 arranged to receive a Pachinko-type single cell trap 108. As shown in FIG. 2C, the lid 206 for the milliwell 104 is larger, and includes a cylindrical lip 212 having a lip height of about 20 μm, a lip width of about 30 μm, and a diameter $\theta_3$ of about 900 microns or larger, depending on a desired size of the tissue sample or crypt to be analyzed. In certain embodiments, a gap may be provided between the bottom part 100 and the top part 200 along a lip 208 of each microwell 210 or lid 204 when the microfluidic device 300 is in a position to permit fluid to flow past or through the array 106 of Pachinko-type single cell traps 108. Additionally, the top part 200 includes one or more fiducials 209-1, 209-2. The bottom part 100 and the top part 200 of FIGS. 1A-2C therefore define pairs of fiducials (109-1, 109-2, 109-3, 209-1, 209-2) for easy alignment on a micrometer scale (e.g., between the open state and the closed state).

FIGS. 3A and 3B illustrate an assembled microfluidic device 300 (based on the design of FIGS. 1A-2C) in an open state and a closed state, respectively. When the array 202 of lids 204 of the top part 200 is aligned with the array 106 of Pachinko-type single cell traps 108, the microfluidic device 300 is in its closed state, as illustrated in FIG. 3B. In such a state, both the milliwell 104 and the microwells 210 are closed and hermetically sealed. When the top part 200 is lifted by 30 microns, then moved to the right so that the array 202 of lids 204 aligns with the receiving chamber 110 and lowered, the microfluidic channel 102 is open (e.g., through the media flow channel ports 207A, 207B) and the in situ cells and/or isolated cells can be exposed to various stimuli, e.g. dissociation media. In the open state of the microfluidic device 300 illustrated in FIG. 3A, cells can also be moved from the milliwell 104 to the Pachinko-type single cell traps 108.

By alternating the two positions of the top part 200 relative to the bottom part 100, one can repetitively switch the microfluidic device 300 from an open position to a closed position (and vice-versa) to enable performance of various experimental steps. In certain embodiments, the closed position is only needed during a relatively brief sensor readout period. The flexibility of permitting the microfluidic device 300 to be switched between an open position and a closed position allows three types of metabolic characterization experiments on the same chip. First, an intact multi-cellular structure is assayed. Second, the multi-cellular structure is dissociated and metabolic measurements of the bulk dissociated cell population are performed in the same milliwell. Thereafter, individual cells are trapped in the Pachinko-type single cell traps 108 and cell metabolism parameters may be measured with single cell resolution.

Alternatively, in certain embodiments, the microfluidic device 300 may be used for metabolic profiling of dissociated cells or cell cultures. To this end, the microfluidic device 300 may be populated with cells by flowing a cell suspension through the microfluidic device 300 with the lid 206 separated from the bottom part 100 by a gap of 20-30 microns. Individual cells are trapped in the array 106 of Pachinko-type single cell traps 108, while a number of cells (e.g., ranging from a few hundred to several thousand or more, depending on cell concentration) populate the milliwell 104.

In certain embodiments, the microfluidic device 300 can be implemented with the milliwell 104 and the array of microwells 210 (or array 202 of lids 204) on the same chip without the above-mentioned single cell traps 108. In such an embodiment, cell loading can be performed by simply depositing an appropriate volume of cell suspension into the microwells 210 using a manual pipette or a robotic liquid handler and letting the cells populate the microwells 210 by gravity settling. After an incubation period, a top layer or chip can be placed on the well-defining bottom layer or chip and transmembrane measurements may be conducted simultaneously on a bulk cell culture of 50 or more cells and individual cells of the same type. This combination provides a unique capability for profiling single cells in isolation and profiling the same type of cells in culture, which is useful for comparative studies of effects of cell-cell communication in a 2D culture.

Figure 4:
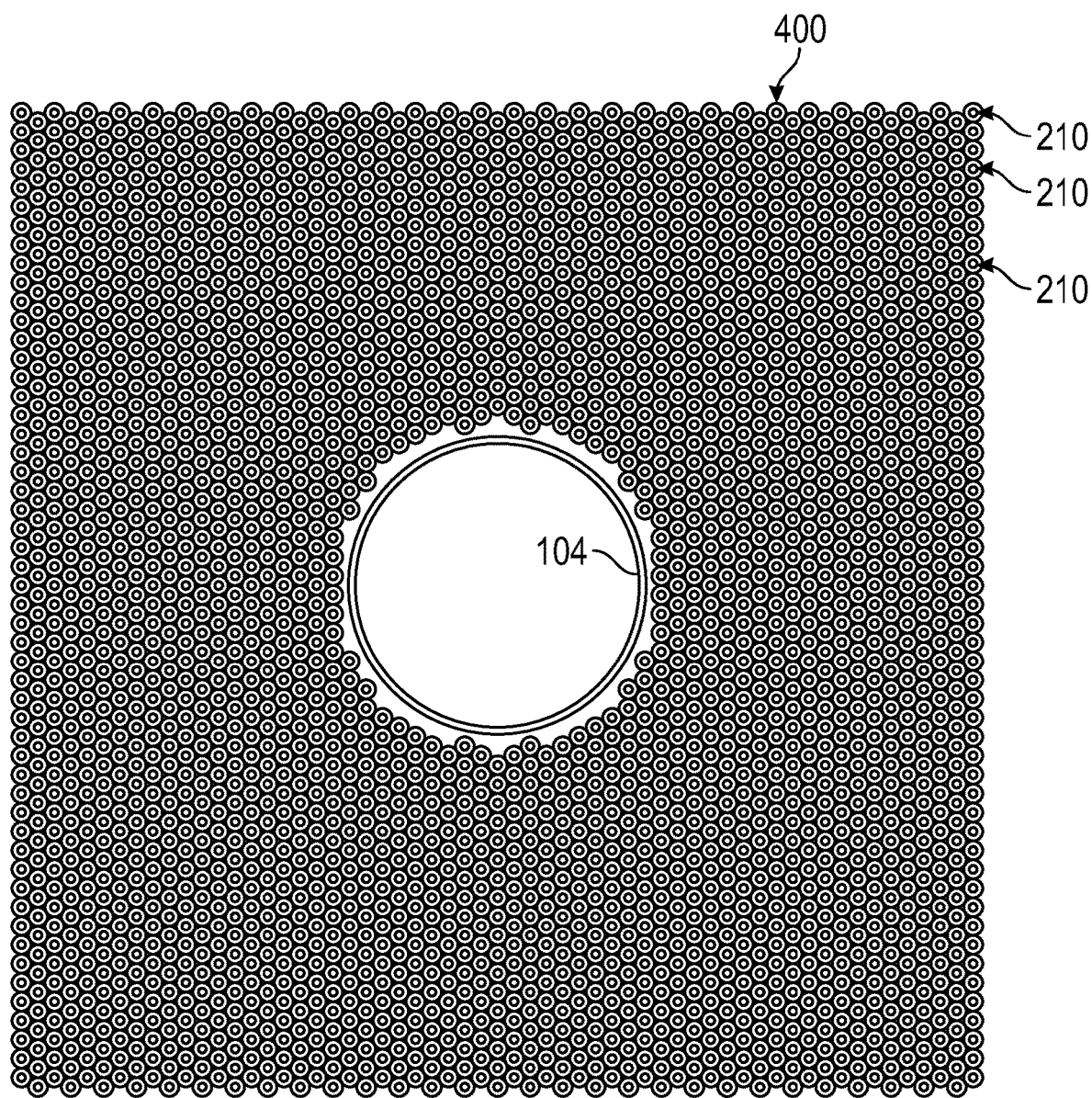
FIG. 4 is a top plan view of a portion of a microfluidic device suitable for mixed single-cell and culture-level measurements.

In certain embodiments, the milliwell 104 may be located at the center of an array of microwells (e.g., with the microwells optionally containing Pachinko-type single cell traps 108) in order to minimize the distance therebetween. Such a configuration is shown in FIG. 4. Minimizing the distance between the milliwell 104 and an array 400 of microwells 210 increases the degree to which the cell population in the milliwell 104 is in diffusional contact with cells in the microwells 210 during incubation. For metabolic flux measurement, where a good seal is required, centering the milliwell 104 as shown in FIG. 4 has the additional advantage of reducing the effect of flexure of the supporting window (through which fluorescence microscopy images are taken) on seal performance. Centering the milliwell 104 also has the advantage of reducing the distance from the edge of the microwell array 400 to the farthest seal point, which affects the time required to conduct a seal test using gas. In certain embodiments, the milliwell 104 should be large enough to accommodate at least 50 cells, but more preferably at least 1,000 or more cells, at the desired confluency. In certain embodiments, multiple milliwells 104 may be used to increase statistical significance. In certain embodiments, the shape of the milliwell(s) 104 does not need to be perfectly circular; instead, the milliwell(s) could be rectangular or any polygonal shape that is conducive to bulk-cell viability.

Figure 5:
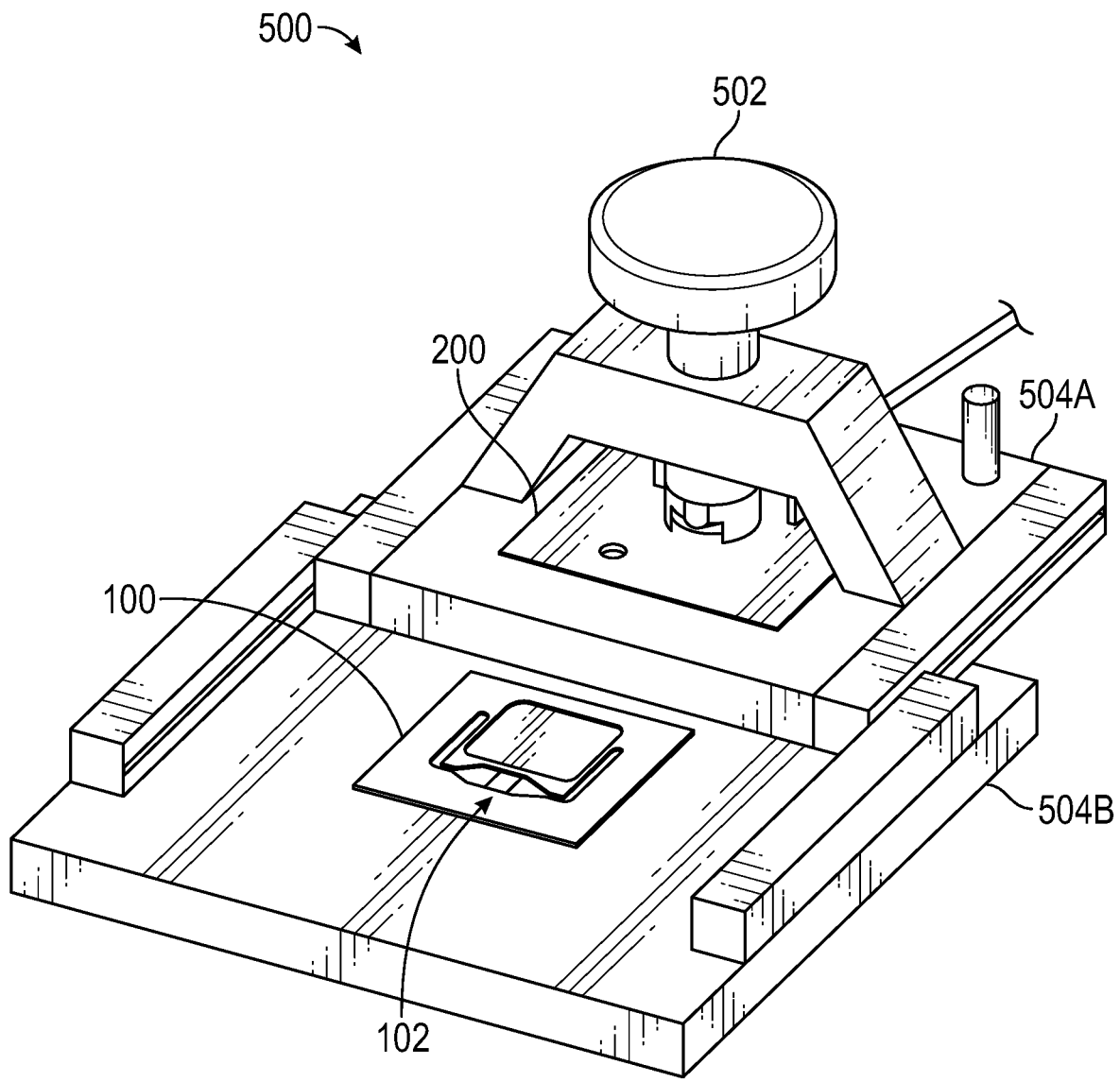
FIG. 5 is a perspective view illustration of a mounting assembly including a translatable portion and incorporating a multi-part microfluidic device as disclosed herein.

FIG. 5 illustrates a mounting assembly 500 suitable for manipulating the two parts of the microfluidic device 300 disclosed herein. The top part 200 of the microfluidic device 300 is pressed against the bottom part 100 by a clamping screw 502 to produce hermetic seals along the microwells 210 and the milliwell 104 (as shown in FIGS. 1A-3B). Washing and media exchange is enabled when an upper part 504A of the mounting assembly 500 is moved relative to a bottom part 504B of the mounting assembly 500, and the microfluidic channel 102 is bounded with the flat portion of the top part 200.

Dissociation represents one of the most demanding steps in terms of sample conservation. To address this, magnetic beads conjugated to appropriate cell surface specific antibodies can be used. For example, one can use an antibody to EpCAM to specifically immobilize epithelial cells. Alternatively, one can use more widely expressed cell surface antigens such as 1 integrin. In certain embodiments, magnetic beads may be introduced to the in situ cells either before or with the addition of enzymatic digestion solution. After incubation, a strong magnet can be placed underneath the milliwell, which at this point contains mostly dissociated cells. The magnetic field forces the cells decorated with magnetic beads to the bottom of the wells, thus preventing their departure during washing steps. After washing, the magnet may be removed to allow the transfer of cells to the array of Pachinko-type single cell traps using a flowing cell medium (e.g., liquid).

Figure 6:
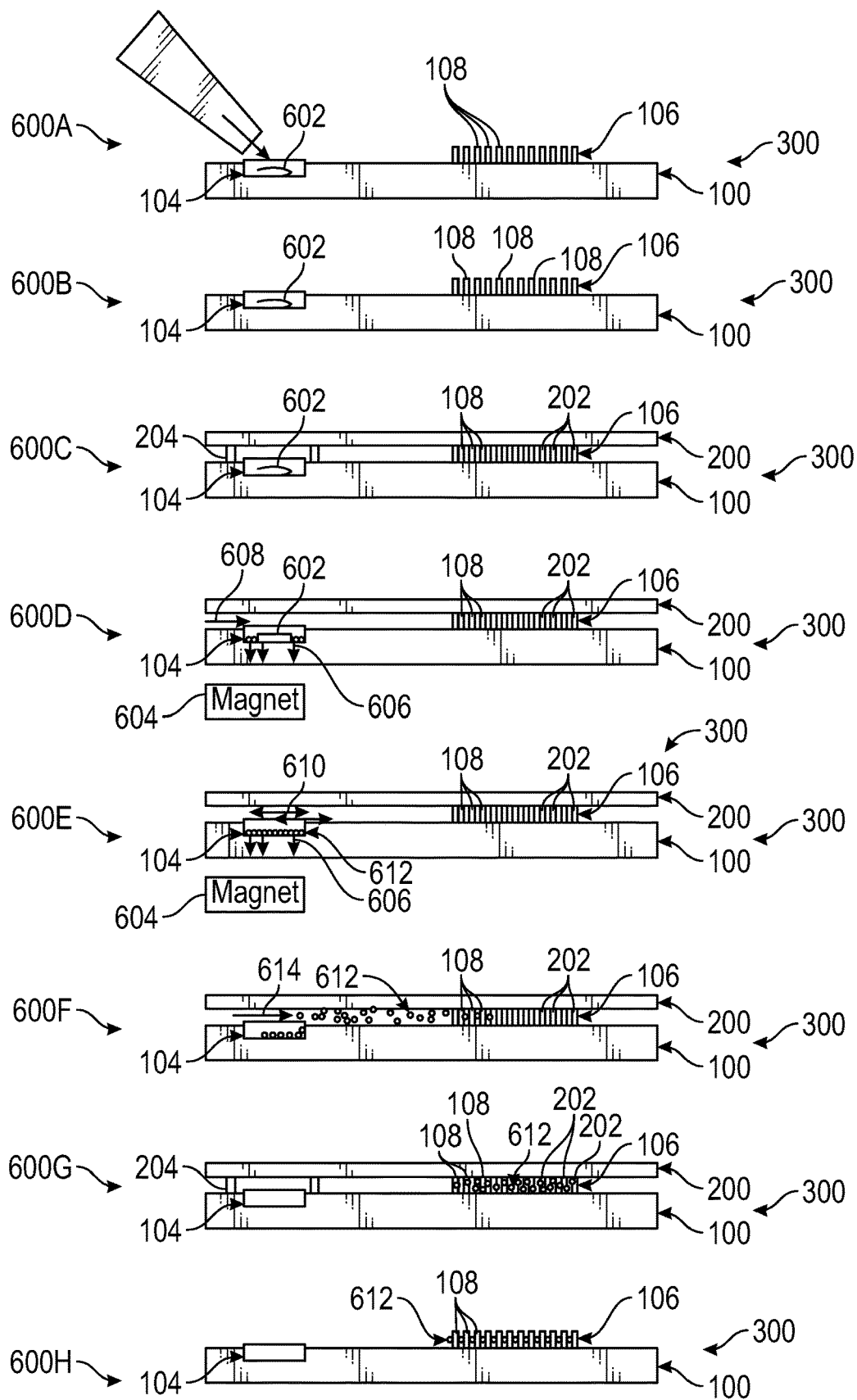
FIG. 6 illustrates performance of eight steps of a multi-parameter functional profiling method, with cross-sectional views of at least portions of a microfluidic device used in performing the method steps.

Detailed steps of an experimental workflow for functional profiling are illustrated in FIG. 6 and proceed as follows. In Step 600A, a cluster of in situ cells 602 (e.g., intact tissue or crypt) is loaded into the milliwell 104. In Step 600B, the cells 602 are incubated for 2-6 hours or longer (e.g., under normal conditions) in the bottom part 100 of the open microfluidic device 300 to allow for attachment and reaching a steady state. In Step 600C, the microfluidic device 300 is closed by addition and compression of the top part 200, and metabolic parameters are measured by exciting the cells and reading out emission intensities of the extracellular sensors in the top part 200. In Step 600D, the microwells 210 are closed and the cells 602 are dissociated using a magnet 604 generating a magnetic force 606 (also referred to as a magnetic field) and by a digestion solution and magnetic beads 608. In particular, the cells 602 are dissociated by enzymatic digestion and immobilized with antibody-conjugated magnetic beads. In Step 600E, the microwells 210 are open and washing is performed on the microfluidic device 300 using a media flush 610 and the magnetic force 606 to prevent escape of bead-associated cells 612 from the milliwell 104. In Step 600F, the microwells 210 are open and the magnetic force 606 is removed to allow single-cell loading into Pachinko-type single cell traps 108 of the array 106 using laminar flow of cell growth medium 614 In Step 600G, the microwells 210 are closed and metabolic parameters of single cells are measured. In (optional) Step 600H, cells of interest 612 are harvested and transcription levels of one or more metabolism-related genes are detected.

Fabrication of the microfluidic device 300 (see FIGS. 1A-3B) according to one embodiment includes the following steps. Hermetically sealable microchambers can be fabricated using conventional lithography and microfabrication techniques to accommodate large (e.g. ~200-300 microns long and 50-100 microns wide) multicellular structures such as small tissue samples or small intestinal crypts. The dimensions of the microchambers can be chosen so as to achieve adequate detection sensitivity with the extracellular sensors. The main criterion determining microchamber design requirements is the time needed for a sample (e.g. a small tissue sample or intestinal crypt) to consume 30% of dissolved oxygen contained in a sealed microchamber. This 30% limit is somewhat arbitrary and based on the performance (signal-to-noise ratio) of the extracellular sensors. To achieve an adequate overall experimental throughput, the average time for a small tissue sample or intestinal crypt to consume one third of the dissolved oxygen in the microchamber may be set to 10 minutes. Based on this requirement and the average oxygen consumption rates of single cells (e.g., Barrett's esophageal epithelial cells) as a starting point, preliminary calculations were conducted for the microchamber physical dimensions. The calculations indicate attainment of the 10 minute measurement duration requirement requires microchamber dimensions of about 200 microns (height)×800 microns (diameter) with a total volume of 100 nL.

After fabrication, the bottom part of the microwells 210 can be coated with a polymer layer such as Parylene C, which serves as an oxygen barrier and facilitates the production of hermetic seals between the top and bottom part 200, 100 of each microchamber (e.g., as shown in FIG. 3B). In certain embodiments, the top part 200 of the microfluidic device 300 can contain one or more circular micropockets with a diameter of about 100 microns for sensor deposition. The top part 200 can be cleaned and the surface functionalized with silane as per standard operation protocols for improved sensor adhesion to the toppart 200. Appropriate sensors can be deposited into the micropockets using non-contact vacuum-assisted deposition, microinjection, or any other technique compatible with sub-nanoliter volume deposition. The surface of the milliwell 104 can be functionalized using extracellular matrix proteins, Matrigel, or any other agents promoting cell adhesion.

Upon reading the foregoing description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A microfluidic device for multiparameter phenotypic profiling of live or fixed individual cells in isolation and within complex multicellular structures in a same assay, the microfluidic device comprising:
    a bottom substrate defining a microfluidic channel containing a plurality of split-walled cell trap structures, wherein the bottom substrate further defines a milliwell arranged for at least selective fluid communication with the microfluidic channel;
    a top substrate defining (i) an array of lids arranged to align with the plurality of split-walled cell trap structures, wherein the array of lids includes an array of lips defining the plurality of microwells, and (ii) a milliwell lid arranged to align with the milliwell;
    wherein one of the bottom substrate or the top substrate is configured to be moved relative to the other of the bottom substrate or the top substrate between a first position and a second position, to permit mating and sealing between at least portions of the bottom substrate and the top substrate; and
    wherein the plurality of split-walled cell trap structures is arranged to be registered with and at least partially received by the plurality of microwells when the microfluidic device is in one of the first position or the second position.

2. The microfluidic device of claim 1, wherein the milliwell comprises a greater volume than the plurality of microwells.

3. The microfluidic device of claim 1, wherein a gap is provided between the bottom substrate and the top substrate along each lip of the array of lips to permit fluid to flow past or through the plurality of split-walled cell trap structures when the microfluidic device is in one of the first position or the second position.

4. The microfluidic device of claim 1, wherein each cell trap structure of the plurality of split-walled cell trap structures comprises an open upstream end sized to receive at least one cell, and comprises a downstream opening configured to inhibit passage of at least one cell while permitting passage of a liquid medium.

5. The microfluidic device of claim 1, wherein each cell trap structure of the plurality of split-walled cell trap structures is configured to receive only a single cell.

6. The microfluidic device of claim 1, further comprising an array of sensors arranged in at least one of the bottom substrate or the top substrate, wherein the array of sensors is in sensory communication with the plurality of microwells.

7. The microfluidic device of claim 1, wherein the milliwell is centrally arranged relative to the plurality of split-walled cell trap structures.

8. The microfluidic device of claim 1, being configured for multi-parameter characterization of cellular phenotypes of cells in tissue or other multicellular structures and the same individual cells in isolation followed by end-point analysis of biomolecular profiles of the same cells.

9. A microfluidic device for multiparameter phenotypic profiling of live or fixed individual cells in isolation and within complex multicellular structures in a same assay, the microfluidic device comprising:
    a first substrate defining a milliwell and an array of microwells, wherein the milliwell comprises a greater volume than each microwell of the array of microwells; and a second substrate including a lid arranged to cover the milliwell and an array of lids to cover the array of microwells;

a plurality of split-walled cell trap structures positioned within a microfluidic channel;

wherein one of the first substrate or the second substrate is configured to be moved relative to the other of the first substrate or the second substrate between a first position and a second position, to permit the milliwell and the array of microwells to be selectively sealed; and wherein the plurality of split-walled cell trap structures is arranged to be selectively registered with and disposed within the array of microwells when the microfluidic device is in one of the first position or the second position.

10. The microfluidic device of claim 9, wherein each cell trap structure of the plurality of split-walled cell trap structures is configured to receive only a single cell.

11. The microfluidic device of claim 9, wherein a gap is provided between the first substrate and the second substrate along a lip of each lid of the array of lids to permit fluid to flow past or through the plurality of split-walled cell trap structures when the microfluidic device is in one of the first position or the second position.

12. The microfluidic device of claim 9, wherein each cell trap structure of the plurality of split-walled cell trap structures comprises an open upstream end sized to receive at least one cell, and comprises a downstream opening configured to inhibit passage of at least one cell while permitting passage of a liquid medium.

13. The microfluidic device of claim 9, further comprising an array of sensors arranged in at least one of the first substrate or the second substrate, wherein the array of sensors is in sensory communication with the array of microwells.

14. The microfluidic device of claim 9, wherein the milliwell is centrally arranged relative to the plurality of split-walled cell trap structures.

15. The microfluidic device of claim 9, being configured for multi-parameter characterization of cellular phenotypes of cells in tissue or other multicellular structures and the same individual cells in isolation followed by end-point analysis of biomolecular profiles of the same cells.

* * * * *